United States Patent
Kim et al.

(10) Patent No.: US 7,745,430 B2
(45) Date of Patent: Jun. 29, 2010

(54) TRANSNASAL ANTICONVULSIVE PHARMACEUTICAL COMPOSITION

(75) Inventors: Kwon Ho Kim, Palisades Park, NJ (US); Paramjeet Kaur, Parsippany, NJ (US); Jae Hoon Jo, Deejeon (KR); Myoung Ki Baek, Daejeon (KR); Yeo Joo Yuk, Seoul (KR)

(73) Assignee: SK Holdings Co., Ltd., Seoul (KR)

( * ) Notice: Subject to any disclaimer, the term of this patent is extended or adjusted under 35 U.S.C. 154(b) by 570 days.

(21) Appl. No.: 11/599,767

(22) Filed: Nov. 15, 2006

(65) Prior Publication Data

US 2008/0113970 A1     May 15, 2008

(51) Int. Cl.
*A61K 31/5513* (2006.01)
*A61K 47/14* (2006.01)

(52) U.S. Cl. ...................... 514/220; 514/785

(58) Field of Classification Search .................. 514/220, 514/785
See application file for complete search history.

(56) References Cited

U.S. PATENT DOCUMENTS

| | | | |
|---|---|---|---|
| 4,863,720 | A | 9/1989 | Burghart et al. |
| 6,627,211 | B1 | 9/2003 | Choi et al. |
| 2002/0032171 | A1* | 3/2002 | Chen et al. ................ 514/54 |

2005/0002987 A1    1/2005   Choi et al.

OTHER PUBLICATIONS

Bechgaard et al. Solubilization of various benzodiazepines for intranasal administration, a pilot study. Pharm. Dev. Tech. 2 (3), 293-96 (1997).*
Moolenaar, et al., International Journal of Pharmaceutics, 5 (1980) 127-137.
Lau and Slatterery (Lau et al., Int. J. Pharm, 54:171-174 (1989).
Li et al. (International Journal of Pharmaceuticals vol. 237, pp. 77-85, 2002.

* cited by examiner

*Primary Examiner*—Frederick Krass
*Assistant Examiner*—Sara E Clark

(57) ABSTRACT

Disclosed herein is a transnasal anticonvulsive pharmaceutical composition comprising diazepam as an active ingredient, water, a fatty acid ester, diethylene glycol monoethyl ether, ethanol and sodium glycocholate, wherein the weight of the fatty acid ester is at least 2-fold higher than that of water and is at least 2-fold higher than that of ethanol.

The anticonvulsive pharmaceutical composition for transmucosal delivery of diazepam according to the present invention includes a minimized content of water and ethanol, a fatty acid ester as a main ingredient and no use of a polar solvent, e.g. glycol, and, exhibits improved diazepam solubility and transmucosal permeability due to using a small amount of water and ethanol. The present invention also includes treatment of convulsions by transnasally administering to a patient in need thereof a therapeutically effective amount of the disclosed compositions.

2 Claims, 2 Drawing Sheets

TRANSNASAL ANTICONVULSIVE PHARMACEUTICAL COMPOSITION

BACKGROUND OF THE INVENTION

1. Field of the Invention

The present invention relates to a transnasal anticonvulsive pharmaceutical composition. More specifically, the present invention relates to an anticonvulsive pharmaceutical composition for transmucosal delivery of diazepam having improved solubility and transmucosal permeability of diazepam.

2. Description of the Related Art

Status epilepticus (SE), a prolonged epileptic seizure, refers to a serious neurological emergency which may lead to the mortality rate of from 3 to 35% in the total SE patients. The primary goal of the treatment of SE resides in the rapid management of pathological seizure activity since the longer that an episode of status epilepticus remains untreated, the more difficult it is to control and the greater the risk of permanent brain damage. Thus, critical to the management of the patients is a prompt treatment involving administration of a pharmaceutical composition in the form of a proper pharmaceutical formulation containing an active drug ingredient at an adequate dose.

Currently, several drug regimens known in the art have been proven to be efficacious in the treatment of status epilepticus. Diazepam is one of the most widely used benzodiazepines for this purpose. Intravenous (IV) administration of anticonvulsants, such as diazepam, is the most rapid way to suppress epileptic convulsions. However, other routes of administration may be highly desirable when intravenous administration is inconvenient or is delayed, for instance, because of technical difficulties such as requirements for sterile equipment and trained personnel, and because of the probable development of phlebitis. In addition, intravenous administration of such medication is often associated with hypotension, cardiac dysrhythmia or central nervous system (CNS) depression. In this connection, Moolenaar et al (Int. J. Pharm., 5: 127-137) have attempted an administration of diazepam to humans via several other routes such as intramuscular injection, oral tablet and rectal solution. Only the rectal administration was found to provide a fairly rapid absorption of the drug and thus, it might be considered as an alternative administration route to IV injection. However, the rectal route is a very inconvenient way of drug administration particularly in the patients requiring emergency treatment.

U.S. Pat. No. 4,863,720, issued to Burghardt, discloses a sublingual sprayable pharmaceutical preparation wherein the active drug ingredient can be a benzodiazepine. Such preparations preferably contain polyethylene glycol (PEG), and ethanol, di- and/or triglycerides of fatty acids and a pharmaceutically acceptable propellant gas are required components.

More recently, it appears that the nasal mucous membrane offers a practical route of administration for therapeutic effects of various medicinal substances. Intranasal administration has an advantage in that drugs of interest may be administered readily and simply to achieve systemic or topical effects, as required. However, the major problem associated with intranasal drug administration is the fact that most drug molecules diffuse poorly and slowly through the nasal mucous membrane and thus the desired level of the therapeutic agent cannot be achieved by means of simple transnasal administration. An additional limitation concerning nasal administration is that it is typically limited to a small volume. That is, it is generally not possible to administer the drug at a dose level of more than approximately 150 µl per nostril. Volumes of the formulation exceeding the above level will be drained out and swallowed into the pharynx. Hence, it is necessary that the required dose of the drug is provided in such a volume.

In addition, it is difficult to develop a pharmaceutical formulation of diazepam suitable for nasal spray administration, due to a low solubility of diazepam in water which is conventionally used to dissolve the drug for administration. Therefore, there is a strong need for the development of a solvent vehicle which can dissolve the desired medication, i.e. diazepam, to a high concentration, while not causing irritability to the nasal mucosa.

The intranasal drug absorption rate can be increased by co-administration of the desired drug with a chemical adjuvant or a penetration enhancer. For example, Lau and Slattery (Lau et al., Int. J. Pharm., 54: 171-174 (1989b)) have attempted an intranasal administration of a benzodiazepine such as diazepam by dissolving it in a variety of solvents such as triacetin, dimethylsulfoxide, PEG 400, Cremophor EL, Lipal-9-LA, isopropyl adipate and Azone.

However, it was found that, while the majority of the solvents dissolved diazepam to the desired concentration, the resulting solutions were too irritating to be used for transnasal administration. Cremophor EL was found to have the lowest irritability for nasal mucosal tissues, but the nasal absorption of the drug with the use of such a vehicle in humans was rather slow ($T_{max}$ of 1.4 hours) and the peak concentration was low, as compared to that observed after IV administration.

In recent years, Li et al (International Journal of Pharmaceutics Vol. 237, pp 77-85, 2002) have disclosed microemulsions for rapid-onset transnasal delivery of diazepam. Further, U.S. Pat. No. 6,627,211 discloses a composition for transnasal administration of diazepam via a solubilized preparation wherein diazepam is dissolved using an aliphatic alcohol, glycol and water as a polar solvent. In addition, US Patent Application No. 2005-0002987 A1 discloses a microemulsion for transnasal administration of diazepam wherein diazepam is dissolved using an emulsion vehicle comprised of equal amounts of a fatty acid and water with the remainder being a hydrophilic surfactant, and a polar solvent, e.g. glycol.

The pharmaceutical preparation disclosed in U.S. Pat. No. 6,627,211 is a solubilized preparation wherein an aliphatic alcohol, a glycol as a polar solvent, and ethanol are used in large amounts. According to this art, when a small amount of diazepam is contained in the preparation, it is possible to enhance the transmucosal permeability of diazepam. However, when the content of diazepam is increased to a level of more than 2.5% as in Example 4 therein, thus resulting in poor dissolution of diazepam and consequently requiring transnasal administration of diazepam in a large volume so as to deliver an effective concentration of the drug, this may lead to the problems associated with a need for repeated administration because a possible maximum amount of intranasal administration is limited to within a level of 150 µl, as discussed hereinbefore. Further, the preparation disclosed in US Patent Application No. 2005-0002987 A1 is a microemulsion preparation using equal amounts of a fatty acid ester and water and large amounts of a hydrophilic surfactant, and a polar solvent, e.g. glycol and an alcohol. According to this art, the concentration of diazepam in the preparation is 41 mg/mL and therefore diazepam can be dissolved up to an about 4.1% concentration, thus resulting in an increased solubility of diazepam as compared to the preparation of U.S. Pat. No. 6,627,211. However, this pharmaceutical formulation suffers from a decreased transmucosal permeability, and therefore also requires transnasal administration of diazepam at a large volume so as to deliver an effective concentration of the drug, thus causing an inconvenience associated with a need of repeated administration. There is thus a need for a pharmaceutical composition for transmucosal administration of diazepam having improved solubility and transmucosal permeability of diazepam. Such compositions and a method of treatment are provided in accordance with the present invention.

SUMMARY OF THE INVENTION

In accordance with an aspect of the present invention, there is provided a transnasal anticonvulsive pharmaceutical composition, comprising diazepam, water, a fatty acid ester, diethylene glycol monoethyl ether, ethanol and sodium glycocholate, wherein the weight of the fatty acid ester is at least 2-fold higher than that of water and is also at least 2-fold higher than that of ethanol. There is also provided a method for treating a convulsion comprising administering a therapeutically effective amount of the above-mentioned pharmaceutical composition to a patient suffering therefrom.

BRIEF DESCRIPTION OF THE DRAWINGS

The present invention will be more clearly understood from the following detailed description taken in conjunction with the accompanying drawings, in which.

DESCRIPTION OF THE PREFERRED EMBODIMENTS

Figure 1:
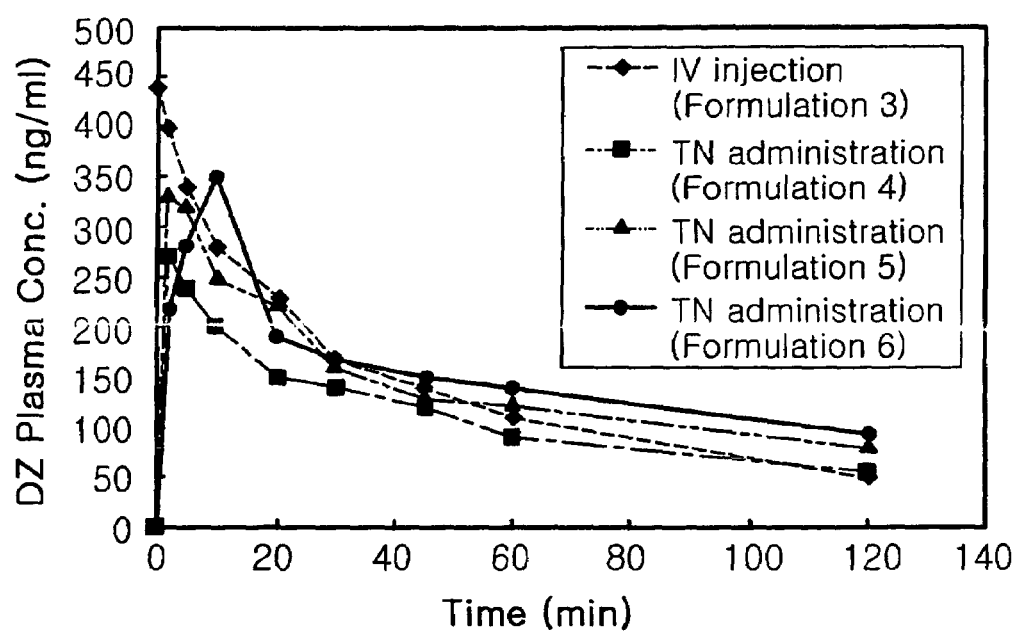
FIG. 1 is a graph showing pharmacokinetic (PK) profiles after intravenous (IV) and transnasal (TN) administration of a conventional diazepam formulation and a diazepam formulation according to the present invention.

The transnasal anticonvulsive pharmaceutical compositions in accordance with the present invention comprise diazepam as an active ingredient, water, a fatty acid ester, diethylene glycol monoethyl ether, ethanol and sodium glycocholate, wherein the weight of the fatty acid ester is at least 2-fold higher than that of water and is also at least 2-fold higher than that of ethanol. The diazepam-containing transnasal anticonvulsive microemulsion formulations of the present invention possess superior characteristics as compared to similar formulations disclosed in the literature as described above.

As a result of a variety of extensive and intensive studies and experiments, the inventors of the present invention have discovered that a diazepam-containing transnasal anticonvulsive microemulsion formulation comprising a minimized content of water and ethanol, a fatty acid ester as a main ingredient and diethylene glycol monoethyl ether exhibits an improved diazepam solubility of up to 6%, as compared to the preparations of U.S. Pat. No. 6,627,211 (2.5%) and US Patent Application No. 2005-0002987 A1 (4.1%), and also exhibits a 2.2-fold increase of the in vitro transmucosal permeability as compared to that of preparations disclosed in U.S. Pat. No. 6,627,211. The present invention has been completed based on these findings.

The pharmaceutical composition of the present invention comprises diazepam as an active ingredient, water, a fatty acid ester, diethylene glycol monoethyl ether, ethanol and sodium glycocholate, wherein the weight of the fatty acid ester is at least 2-fold higher than that of water and is also at least 2-fold higher than that of ethanol. Reducing the weight of the fatty acid ester below these levels may undesirably result in a loss of transparency and decreased stability of the resulting microemulsion. Preferably, the amount of the fatty acid ester in the composition is from about 2 to 4 times the weight of water present and is from about 2 to 3.5 times the weight of ethanol.

Diazepam, an anticonvulsive active ingredient contained in the composition of the present invention, is preferably contained in an amount of from about 0.1 to 10.0% by weight, based on the total weight of the composition, but is not limited thereto.

Examples of the fatty acid esters that can be used in the present invention include caprylocaproyl macrogol-8-glycerides and ethyl laurate. These materials may be used alone or in any combination. The fatty acid ester is preferably contained in an amount of more than about 30% by weight and more preferably from about 35 to 45% by weight, based on the total weight of the composition. Most preferably, the fatty acid ester is contained in a range of from about 38 to 42% by weight, based on the total weight of the composition. Preferably, the fatty acid ester is a mixture of caprylocaproyl macrogol-8-glycerides and ethyl laurate in a weight ratio of 4.5:3.5 to 5.5:2.5.

The sum of water and ethanol is preferably from about 20 to 30% by weight, based on the total weight of the composition. Sodium glycocholate is preferably contained in an amount of from about 0.5 to 1.2% by weight, based on the total weight of the composition.

Diethylene glycol monoethyl ether is preferably contained in an amount of from about 30 to 45% by weight, based on the total weight of the composition. Diethylene glycol monoethyl ether that can be used in the present invention is commercially available and may include, for example Transcutol P (trade name, produced and sold by Gattefosse, Westwood, N.J., USA).

In one preferred embodiment, the transnasal anticonvulsive pharmaceutical composition of the present invention is comprised of from about 4 to 6% by weight of diazepam, from about 8 to 12% by weight of water, from about 35 to 45% by weight of fatty acid ester, from about 30 to 45% by weight of diethylene glycol monoethyl ether and from about 12 to 17% by weight of ethanol.

The subject emulsions are formed by conventional techniques. For example, the oil (ethyl laurate) and surfactant/cosurfactant (Transcutol/caprylocaproyl macrogol-8-glycerides/ethanol) are accurately weighed and mixed thoroughly under the proper mixing of a magnetic stirrer to form a transparent and homogenous mixture. The oil/surfactant/cosurfactant mixture is then titrated with an accurate amount of distilled water in a drop-wise addition under constant and thorough mixing, e.g. under sonication, to form a clear microemulsion. One gram of sodium glycocholate (SGC; Sigma-Aldrich) is dissolved in a sufficient amount of the above basic microemulsion to make 100 mL, being 1% w/v of SGC. Diazpam is incorporated in the microemulsion by dissolving the weighed amount of the drug powder (e.g., 2 g, 4 g, and 6 g) into a sufficient amount of 1% SGC (w/v)/ME to make a total 100 mL of a clear drug microemulsion preparation The utilization of the transnasal anticonvulsive pharmaceutical composition of the present invention greatly facilitates administration of the drug. As compared with parenteral administration, for example, a simple sprayer, dropper or nebulizer will provide prompt and convenient delivery of the medicaments, in particular, for the emergency treatment of acute convulsive episodes of epilepsy. From a clinical point of view, transnasal administration often provides an improved duration of anticonvulsive effects. According to the present invention, the therapeutic effects and duration of the drug can be more efficiently and accurately controlled by a single- and multiple-dose administration of the preparation of the invention. Even though the present invention has been described with respect to an anticonvulsant as a model compound, it will be appreciated that it is also applicable to other biologically active agents that may be administered to various mucous membranes of humans and animals.

EXAMPLES

Now, the present invention will be described in more detail with reference to the following examples. These examples are provided only for illustrating the present invention and should not be construed as limiting the scope and spirit of the present invention.

Example 1

In Vitro Nasal Mucous Membrane Permeation Study

The nasal mucous membrane used in the in vitro experiment was obtained from New Zealand White rabbits, weighing 2.5 to 3.0 kg. Rabbits were sacrificed by intravenous (IV) injection of pentobarbital sodium. The nasal septum was carefully removed from a bone block using surgical scissors and a bone-cutting saw. Two pieces of the nasal mucous membrane were then carefully stripped from the nasal septum without touching the center of the membrane surface and washed with a normal saline solution. The mucous membrane was mounted between two half-cells of a glass diffusion cell system. The exposed area of the nasal mucous membrane was approximately $0.196 \, cm^2$. A test solution or suspension (3.5 mL) was introduced into the mucosal side of the membrane in the donor compartment while 3.5 mL of a mixture of 10% ethanol, 40% propylene glycol and 50% isotonic phosphate buffer solution (pH 7.4) was added to the receptor compartment. The entire diffusion system was maintained at 37° C. throughout the experiment.

At predetermined time intervals, 100 µl of the receptor solution was withdrawn for the assay and refilled with an equal volume of a fresh receptor medium to keep the volume constant. The steady-state flux value was calculated from the linear slope obtained by plotting a cumulative amount of a drug permeated as a function of time. Each experiment was carried out in at least duplicate.

In order to determine an amount of diazepam contained in the receptor medium, this study has employed a high-pressure liquid chromatography system equipped with a multi-solvent delivery system (Model 600E, Waters Associates, Milford, Mass., USA), an auto-injector (Model 717 Plus, Waters Associates), a photodiode array detector (Model 996, Waters Associates), a reverse phase symmetric $C_{18}$ column (150 mm×3.9 mm ID, 5 µm), and a Millenium 2010 software computer system. The mobile phases and UV wavelengths utilized for the analysis of diazepam were 70% methanol and 30% water at 254 nm; 60% methanol and 40% water at 252 nm; and 25% acetonitrile and 75% water at 262 nm, respectively. This experimental method was used in Example 3.

Example 2

Preparation of Diazepam Formulations

For comparison of transmucosal permeability of a drug in rabbits, the transnasal preparation disclosed in U.S. Pat. No. 6,627,211 (Formulation 1) and a microemulsion preparation using a vehicle system of the present invention (Formulation 2) were prepared. Both preparations were formulated to contain an equal weight of diazepam. For a transmucosal permeation experiment, the diazepam preparation of U.S. Pat. No. 6,627,211 was prepared by adding 1% sodium glycocholate to a co-solvent vehicle consisting of 30% ethanol (ETOH), 60% propylene glycol (PG) and 10% water (WT), followed by addition of 1% diazepam (Formulation 1). A preparation containing 1% diazepam was prepared using a microemulsion vehicle system (see Table 1) of the present invention (Formulation 2). As caprylocaproyl macrogol-8-glycerides, Labrasol (available from Gattefosse, Westwood, N.J., USA) was used. As diethyl glycol monoethyl ether, Transcutol P (available from Gattefosse, Westwood, N.J., USA) was used. Other reagents including ethyl laurate, ethanol and sodium glycocholate were purchased from Sigma Chemical.

TABLE 1

| Composition of Formulation 2 | |
|---|---|
| Ingredients | Contents (wt %) |
| Caprylocaproyl macrogol-8-glycerides, | 25.0 |
| Diethyl glycol monoethyl ether | 37.5 |
| Ethyl laurate | 15.0 |
| Ethanol | 12.5 |
| Distilled water | 10.0 |
| Sodium glycocholate | 1.0 |

Example 3

This example is intended for the in vitro permeation study of diazepam through the freshly excised nasal membrane. In this study, the transmucosal permeability was compared between Formulation 1 for transnasal administration proposed in U.S. Pat. No. 6,627,211 as described above and Formulation 2 according to the present invention.

TABLE 2

| Transmucosal permeability of transnasal formulations | |
|---|---|
| Formulations | Permeability Jss ($\mu g/cm^2/hr$) |
| Formulation 1 (U.S. Pat. No. 6,627,211) | 89.7 ± 10.1 |
| Formulation 2 (Vehicle of Invention) | 196.6 ± 4.9 |

Example 4

Preparation of Diazepam Formulations

The bioavailability of the preparation of the present invention containing diazepam was tested after intranasal application to New Zealand White rabbits (n=3-4). For comparison, the bioavailability of a diazepam injection was examined in vivo after intravenous administration at a dose of 1 mg/kg. This injectable formulation (10 mg/2 mL) was purchased from Elkins-Sinn, Inc. (Cherry Hill, N.J., USA) which was prepared with propylene glycol (0.4 mL), alcohol (0.1 mL), benzyl alcohol (0.015 mL), sodium benzoate/benzoic acid (50 mg), and water for injection q.s. to make a volume of 1 mL (Formulation 3).

For comparison, a transnasal preparation of U.S. Pat. No. 6,627,211 (Formulation 4, 2% diazepam), a transnasal preparation of US Patent Application No. 2005-0002987 A1 (Formulation 5, 4% diazepam) and a microemulsion preparation using a vehicle system of the present invention (Formulation 6, 6% diazepam) were prepared, respectively. All of the preparations were formulated to contain diazepam in an amount by weight showing a maximum solubility.

For transmucosal permeation experiments, the diazepam preparation of U.S. Pat. No. 6,627,211 was prepared by adding 1% sodium glycocholate to a co-solvent vehicle consisting of 30% ethanol (ETOH), 60% propylene glycol (PG) and 10% water (WT), followed by addition of 2% diazepam (Formulation 4). In addition, the diazepam preparation of US Patent Application No. 2005-0002987 A1 was prepared by adding 4% diazepam to a microemulsion vehicle consisting of 15% ethyl laurate, 23.3% polysorbate-80, 23.3% propylene glycol, 23.4% ethanol and 15% water, according to Formula A of Examples thereof (Formulation 5). A preparation containing 6% diazepam was prepared as described in Example 2 using a microemulsion vehicle system of the present invention (Formulation 6).

Example 5

Bioavailability of Diazepam Formulations

Just prior to the experiment, rabbits in groups of three or four were weighed and restrained in rabbit restrainers. For intravenous (IV) injection administration, rabbits received 1 mg/kg of diazepam via an ear-vein infusion of Formulation 3 for 20 sec. For transnasal (TN) administration, each rabbit has received 2 mg/kg of diazepam by spraying the required volumes of Formulations 4, 5 and 6 into each nostril of animals within 5 sec, using a Pfeiffer spray device.

Blood samples (1 mL) were collected from ear veins of rabbits at time points of 0, 2, 5, 10, 20, 30, 45, 60, and 120 min after the IV and TN administration. Plasma was separated from the blood samples by centrifugation and stored at −20° C. until analyzed.

For analysis, plasma samples (0.5 mL) were accurately transferred into 1.5 mL polypropylene centrifuge tubes. After adding methanol (0.5 ml) and acetonitrile (0.5 ml) to the plasma samples, the mixture was vortexed for 30 sec and centrifuged at 4000 rpm for 10 min. The plasma concentration of diazepam was analyzed by HPLC. The analysis was performed with the Waters HPLC as described in Example 1. The column used in this study was a 3.9 mm×150 mm×5 μm symmetric $C_{18}$ column. The mobile phase was a mixture of 50% methanol, 10% acetonitrile and 40% phosphate buffer (pH 3.5) (v/v). The flow rate of the mobile phase was 1 mL/min and the UV detection was made at 229 nm. The detection limit for diazepam was 15 ng/mL. The area (AUC) under the drug-plasma concentration-time curve, from 0 min to 60 min, was calculated by the linear trapezoidal method.

The bioavailability data obtained in this manner is given in Table 3 below. The bioavailability and pharmacokinetic profiles, obtained after administration of a single IV administration preparation (Formulation 3), Formulations 4 and 5 for transnasal administration of diazepam according to the conventional prior art and the transnasal preparation of the present invention (Formulation 6), are depicted in FIG. 1.

As can be seen from the results of Table 3 below, the bioavailability of Formulation 4 is higher than that of Formulation 6. However, as discussed hereinbefore, a maximum diazepam solubility of Formulation 4 is about 2% and that of Formulation 5 is about 4%, whereas that of Formulation 6 is about 6%. Therefore, Formulations 4 and 5 require transnasal administration two times or more so as to exert desired therapeutic effects, whereas Formulation 6 can exhibit desired effects even with a single transnasal administration and therefore is significantly advantageous for market commercialization.

TABLE 3

Bioavailability of transnasal formulations over 1 hour

| Formulations | Bioavailability (F, %)[b] |
|---|---|
| Formulation 3 (for injection, IV)[a] | 100 |
| Formulation 4 (U.S. Pat. No. 6,627,211) | 65.0 |
| Formulation 5 (US Patent Application No. 2005-0002987 A1) | 50.3 |
| Formulation 6 (Vehicle of Invention) | 56.2 |

[a]IV Formulation 3: 0.5% Diazepam Injection, USP, Elkins-Sinn, Inc. (PG/ETOH/Benzyl Alcohol/Sodium Benzoate/Benzoic Acid/Water for Injection)
[b]AUC: Area under curve, for 1 hour
Normalized data determined using the following equation:
$F = AUC_{IN, 2\ mg,\ 1\ hr}/(2 \times AUC_{IV,\ 1\ mg,\ 1\ hr}) \times 100$

Example 6

Study of Diazepam Distribution in Various Brain Regions of Rabbits

Immediately prior to the experiment, rabbits were weighed and restrained in rabbit restrainers. Thirty rabbits were divided into two groups, i.e., an intravenous (IV) injection group and a transnasal (TN) administration group, each consisting of 15 animals divided into five subgroups of three animals each. For the IV injection group, rabbits received 1 mg/kg of diazepam via an ear-vein infusion of Formula 3 for 20 sec. For the TN administration group, each rabbit has received 2 mg/kg of diazepam by spraying Formulation 6 into each nostril of animals within 5 sec, using a Pfeiffer spray device. Brain samples were respectively collected at time points of 5, 10, 20, 40 and 60 minutes after the IV injection (Formulation 3) and TN administration (Formulation 6). Three animals were used for each sampling time.

Plasma samples (each 3 mL) were collected from ear veins of rabbits at the same time points. Thereafter, animals were sacrificed, and 1 mL of cerebral spinal fluid (CSF) was collected using a cisternal puncture. Then, the brain was isolated from the cranium of the animal. The thus-isolated brain was immediately washed with physiological saline to remove the clotted blood, wiped with Kimberly-Clarks wipe, and immediately stored at −40° C. until analyzed.

For analysis, the rabbit brain was divided into 6 regions: olfactory bulb (OB), olfactory tract (OT), anterior section of cerebrum (CB1), middle section of cerebrum (CB2), posterior section of cerebrum (CB3) and cerebellum (CL).

Among the thus-isolated brain regions, the cerebrum including CB1, CB2 and CB3 sections accounts for 72.4% of the total brain volume, and cerebellum (CL) accounts for 20.3%. The olfactory tract (OT) and olfactory bulb (OB) account for 4.7% and 2.6% of the total brain volume, respectively. The total brain weight of individual rabbits weighing 2.5 to 3 kg is in the range of 7 to 10 g, which corresponds to 0.3% of the total body weight. For accurate analysis, each brain region was carefully separated and subjected to the weight determination within an error range of ±0.1 mg.

The analysis was made for plasma, CSF and brain tissue samples using solid phase extraction (SPE), during which diazepam was extracted using an Oasis-HLB cartridge.

In order to determine the content of diazepam in the plasma, CSF and brain tissue samples, LC/MS (Perkin Elmer Sciex API 150EX mass spectrometer) was used. After 10 min corresponding to the second point of total 5 sampling time points, the concentration of diazepam in the plasma, CSF and brain tissue of the rabbit was determined and is shown in FIG. 2.

Figure 2:
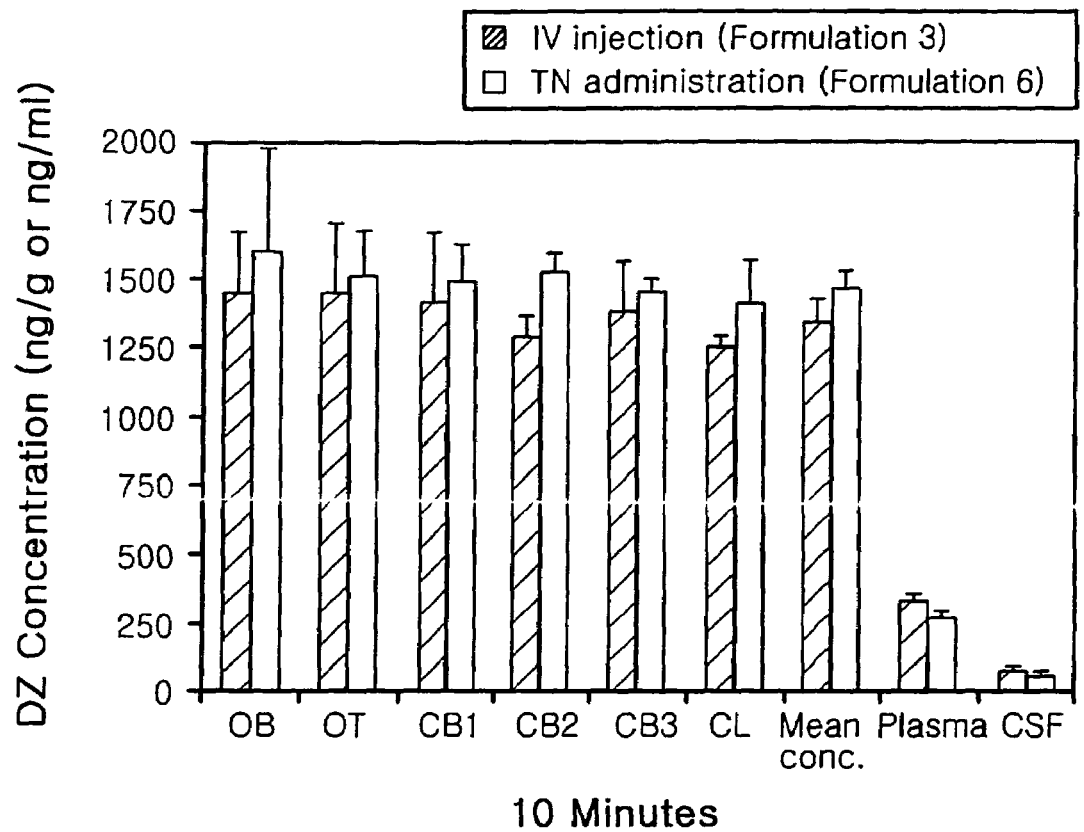
FIG. 2 is a bar graph showing a diazepam concentration in various brain regions of a rabbit after intravenous (IV) and transnasal (TN) administration of a transnasal diazepam formulation according to the present invention.

From the results given in FIG. 2, it can be seen that diazepam of each sample has reached a similar concentration 10 min after IV injection and TN administration.

Example 7

Chemical Stability Study

In order to confirm the stability of the drug in the pharmaceutical composition according to the present invention, a stability study was performed on Formulation 6 of Example 4 at different storage temperatures of 7° C., 25° C. and 45° C. over a 20-week time period.

Samples were collected at predetermined time intervals, and a diazepam concentration was determined by means of an HPLC method of Example 1. The chemical stability data determined in terms of the percent drug recovery is given in Table 4 below.

TABLE 4

Chemical stability of diazepam in the formulation of the Invention (Formulation 6).

| Time (Weeks) | Retention (%, 7° C.) | Retention (%, 25° C.) | Retention (%, 45° C.) |
| --- | --- | --- | --- |
| Starting point (zero time) | 100.0 | 100.0 | 100.0 |
| 1 | 100.5 | 100.1 | 100.3 |
| 2 | 100.6 | 100.7 | 100.4 |
| 3 | 100.4 | 100.3 | 100.2 |
| 4 | 100.0 | 100.2 | 100.0 |
| 6 | 100.9 | 100.1 | 100.1 |
| 8 | 100.7 | 100.4 | 100.3 |
| 20 | 100.2 | 100.1 | 99.9 |

From the results of Table 4, it can be confirmed that the transnasal formulation of diazepam according to the present invention is chemically stable at storage temperatures of 7° C. 25° C. and 45° C. for 20 weeks.

The transnasal anticonvulsive compositions of conventional prior art U.S. Pat. No. 6,627,211 and US Patent Application No. 2005-0002987 A1 have required repeating administration more than two times so as to reach a therapeutically effective concentration of diazepam, whereas the transnasal anticonvulsive composition of the present invention can reach a therapeutically effective concentration of diazepam even with a single administration and is therefore meaningful in that the convenience of use for patients is significantly enhanced.

As apparent from the above description, the anticonvulsive pharmaceutical composition for transmucosal delivery of diazepam according to the present invention comprises a minimized content of water and ethanol, a fatty acid ester as a main ingredient and diethylene glycol monoethyl ether, and exhibits improved diazepam solubility and transmucosal permeability by using a small amount of water and ethanol.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A transnasal anticonvulsive pharmaceutical composition comprising from about 4 to 6% by weight of diazepam as an active ingredient, from about 8 to 12% by weight of water, a fatty acid ester, from about 30 to 45% by weight of diethylene glycol monoethyl ether, from about 12 to 17% by weight of ethanol and from about 0.5 to 1.2% by weight of sodium glycocholate, wherein the weight of the fatty acid ester is at least 2-fold higher than that of water and is at least 2-fold higher than that of ethanol, the fatty acid ester is contained in an amount of from about 38 to 42% by weight, based on the total weight of the composition, and is a mixture of caprylocaproyl macrogol-8-glycerides and ethyl laurate in a weight ratio of from 4.5:3.5 to 5.5:2.5.

2. A method for treating a convulsion, comprising administering a therapeutically effective amount of the pharmaceutical composition of claim 1 to a patient suffering from the convulsion.

* * * * *